(12) United States Patent
Bukesov et al.

(10) Patent No.: US 12,220,166 B2
(45) Date of Patent: Feb. 11, 2025

(54) TARGET IDENTIFICATION WITH OPTICAL FEEDBACK SIGNAL SPLITTER

(71) Applicant: GYRUS ACMI, INC., Westborough, MA (US)

(72) Inventors: Sergey A. Bukesov, Acton, MA (US); Kurt G. Shelton, Bedford, MA (US); Brian M. Talbot, Southborough, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

(21) Appl. No.: 18/332,072

(22) Filed: Jun. 9, 2023

(65) Prior Publication Data
US 2023/0310076 A1 Oct. 5, 2023

Related U.S. Application Data

(63) Continuation of application No. 18/055,486, filed on Nov. 15, 2022, which is a continuation of application
(Continued)

(51) Int. Cl.
*A61B 18/18* (2006.01)
*G02B 27/12* (2006.01)
(Continued)

(52) U.S. Cl.
CPC ............ *A61B 18/18* (2013.01); *G02B 27/123* (2013.01); *G02B 27/141* (2013.01); *H04B 10/25* (2013.01);
(Continued)

(58) Field of Classification Search
CPC ............ A61B 1/00013; A61B 1/00165; A61B 1/043; A61B 18/18; A61B 18/26;
(Continued)

(56) References Cited

U.S. PATENT DOCUMENTS

| | | | |
|---|---|---|---|
| 6,174,291 | B1 | 1/2001 | McMahon et al. |
| 6,554,824 | B2 | 4/2003 | Davenport et al. |

(Continued)

FOREIGN PATENT DOCUMENTS

| | | |
|---|---|---|
| CN | 101622566 | 1/2010 |
| CN | 104603601 | 5/2015 |

(Continued)

OTHER PUBLICATIONS

"Anti-reflective coating", Wikipedia, [Online]. Retrieved from the Internet: <URL: https://en.wikipedia.org/wiki/Anti-reflective_coating>, (May 29, 2021), 10 pgs.
(Continued)

*Primary Examiner* — Scott Luan
(74) *Attorney, Agent, or Firm* — Schwegman Lundberg & Woessner, P.A.

(57) ABSTRACT

A probe of a target identification system can be extended via a first lumen of a viewing instrument, such as for illuminating an area beyond a distal end of the viewing instrument via an optical path of the viewing instrument. An optical response to the illumination of the area can be received via an optical path of the probe and can be split from other optical signals of the optical path. The optical response information can be used to identify characteristics of a target and to adjust parameters of a working instrument such as a working instrument contemporaneously using the probe.

20 Claims, 9 Drawing Sheets

Related U.S. Application Data

No. 16/984,447, filed on Aug. 4, 2020, now Pat. No. 11,523,865.

(60) Provisional application No. 63/018,262, filed on Apr. 30, 2020, provisional application No. 63/008,940, filed on Apr. 13, 2020, provisional application No. 62/931,360, filed on Nov. 6, 2019, provisional application No. 62/882,837, filed on Aug. 5, 2019.

(51) Int. Cl.

| | | |
|---|---|---|
| *G02B 27/14* | (2006.01) | |
| *H04B 10/25* | (2013.01) | |
| *H04B 10/50* | (2013.01) | |
| *H04B 10/60* | (2013.01) | |
| *A61B 18/00* | (2006.01) | |
| *A61B 18/20* | (2006.01) | |
| *A61B 18/22* | (2006.01) | |
| *A61B 18/26* | (2006.01) | |

(52) U.S. Cl.
CPC .......... *H04B 10/503* (2013.01); *H04B 10/60* (2013.01); *A61B 2018/00577* (2013.01); *A61B 2018/00982* (2013.01); *A61B 2018/20355* (2017.05); *A61B 2018/20361* (2017.05); *A61B 2018/2205* (2013.01); *A61B 2018/2261* (2013.01); *A61B 2018/2266* (2013.01); *A61B 2018/2277* (2013.01); *A61B 18/26* (2013.01)

(58) Field of Classification Search
CPC .......... A61B 2018/00577; A61B 2018/00982; A61B 2018/20355; A61B 2018/20361; A61B 2018/2205; A61B 2018/2261; A61B 2018/2266; A61B 2018/2277; A61B 5/0036; A61B 5/0075; A61B 5/0084; A61B 5/4836; A61B 5/6852; G02B 27/123; G02B 27/141; H04B 10/25; H04B 10/503; H04B 10/60
See application file for complete search history.

(56) References Cited

U.S. PATENT DOCUMENTS

| | | | |
|---|---|---|---|
| 9,017,316 | B2 | 4/2015 | Khatchaturov et al. |
| 9,445,871 | B2 | 9/2016 | Kang et al. |
| 9,486,286 | B2 | 11/2016 | Hodel et al. |
| 9,757,199 | B2 | 9/2017 | Chia et al. |
| 9,949,615 | B2 | 4/2018 | Zappia et al. |
| 9,968,403 | B2 | 5/2018 | Hasenberg et al. |
| 10,039,604 | B2 | 8/2018 | Chia et al. |
| 10,067,304 | B2 | 9/2018 | Yu et al. |
| 10,105,184 | B2 | 10/2018 | Beck et al. |
| 10,175,435 | B2 | 1/2019 | Peng et al. |
| 10,258,415 | B2 | 4/2019 | Harrah et al. |
| 10,383,690 | B2 | 8/2019 | Hodel et al. |
| 11,406,447 | B2 | 8/2022 | Bukesov et al. |
| 11,523,865 | B2 | 12/2022 | Bukesov et al. |
| 2002/0045811 | A1 | 4/2002 | Kittrell et al. |
| 2011/0037987 | A1 | 2/2011 | Gurny et al. |
| 2012/0184827 | A1* | 7/2012 | Shwartz .................. A61B 5/418 356/402 |
| 2012/0327423 | A1 | 12/2012 | Hanebuchi |
| 2015/0224249 | A1 | 8/2015 | Ciulla et al. |
| 2015/0230864 | A1 | 8/2015 | Xuan et al. |
| 2015/0272674 | A1 | 10/2015 | Xuan et al. |
| 2015/0272679 | A1 | 10/2015 | Wang et al. |
| 2016/0081749 | A1 | 3/2016 | Zhang et al. |
| 2016/0166319 | A1 | 6/2016 | Yu et al. |
| 2017/0173275 | A1 | 6/2017 | Anderson et al. |
| 2018/0092693 | A1 | 4/2018 | Falkenstein et al. |
| 2018/0263695 | A1* | 9/2018 | Kim ..................... A61B 5/01 |
| 2019/0113700 | A1 | 4/2019 | Peng et al. |
| 2019/0151022 | A1 | 5/2019 | Yu et al. |
| 2019/0159839 | A1 | 5/2019 | Zhang et al. |
| 2019/0192237 | A1 | 6/2019 | Harrah et al. |
| 2019/0246908 | A1 | 8/2019 | Pyun et al. |
| 2019/0298449 | A1 | 10/2019 | Khachaturov et al. |
| 2019/0393669 | A1 | 12/2019 | Yu et al. |
| 2021/0038300 | A1 | 2/2021 | Bukesov et al. |
| 2021/0190585 | A1 | 6/2021 | Valouch et al. |
| 2021/0338325 | A1 | 11/2021 | Bukesov et al. |
| 2023/0075714 | A1 | 3/2023 | Bukesov et al. |

FOREIGN PATENT DOCUMENTS

| | | |
|---|---|---|
| CN | 114340536 A | 4/2022 |
| CN | 114340536 B | 7/2024 |
| DE | 112020003748 T5 | 4/2022 |
| EP | 3510962 A1 | 7/2019 |
| EP | 3512448 A1 | 7/2019 |
| EP | 3522811 A1 | 8/2019 |
| JP | H09117407 A | 5/1997 |
| JP | 2022543289 A | 10/2022 |
| JP | 2024100979 A | 7/2024 |
| WO | WO-1990014797 A1 | 12/1990 |
| WO | WO-2011021419 A1 | 2/2011 |
| WO | 2018115415 | 6/2018 |
| WO | 2019115595 | 6/2019 |
| WO | WO-2020033121 A1 | 2/2020 |
| WO | WO-2021026145 A1 | 2/2021 |

OTHER PUBLICATIONS

"U.S. Appl. No. 16/984,447, Non Final Office Action mailed Feb. 8, 2022", 9 pgs.

"U.S. Appl. No. 16/984,447, Notice of Allowance mailed Aug. 10, 2022", 9 pgs.

"U.S. Appl. No. 16/984,447, Response filed Apr. 14, 2022 to Non Final Office Action mailed Feb. 8, 2022", 13 pgs.

"U.S. Appl. No. 16/984,447, Response filed Dec. 3, 2021 to Restriction Requirement mailed Oct. 4, 2021", 9 pgs.

"U.S. Appl. No. 16/984,447, Restriction Requirement mailed Oct. 4, 2021", 7 pgs.

"U.S. Appl. No. 17/376,958, Examiner Interview Summary mailed Dec. 16, 2021", 2 pgs.

"U.S. Appl. No. 17/376,958, Non Final Office Action mailed Sep. 16, 2021", 12 pgs.

"U.S. Appl. No. 17/376,958, Notice of Allowance mailed Jan. 20, 2022", 8 pgs.

"U.S. Appl. No. 17/376,958, Notice of Allowance mailed Apr. 6, 2022", 8 pgs.

"U.S. Appl. No. 17/376,958, Response filed Dec. 14, 2021 to Non Final Office Action mailed Sep. 16, 2021", 13 pgs.

"U.S. Appl. No. 18/055,486, Restriction Requirement mailed Jul. 24, 2023", 7 pgs.

"Indian Application Serial No. 202247004810, First Examination Report mailed Jun. 17, 2022", 6 pgs.

"Indian Application Serial No. 202247004810, Response filed Dec. 16, 2022 to First Examination Report mailed Jun. 17, 2022", 25 pgs.

"International Application Serial No. PCT/US2020/044871, International Preliminary Report on Patentability mailed Feb. 17, 2022", 8 pgs.

"International Application Serial No. PCT/US2020/044871, International Search Report mailed Oct. 29, 2020", 5 pgs.

"International Application Serial No. PCT/US2020/044871, Written Opinion mailed Oct. 29, 2020", 6 pgs.

"Japanese Application Serial No. 2022-507462, Notification of Reasons for Refusal mailed Feb. 7, 2023", w/ English Translation, 7 pgs.

"Japanese Application Serial No. 2022-507462, Office Action mailed Jul. 4, 2023", w/ English Translation, 12 pgs.

"Japanese Application Serial No. 2022-507462, Response filed May 10, 2023 to Notification of Reasons for Refusal mailed Feb. 7, 2023", with English claims, 16 pgs.

"Thorlabs, Inc.—Your Source for Fiber Optics, Laser Diodes, Optical Instrumentation and Polarization Measurement & Control",

(56) References Cited

OTHER PUBLICATIONS

[Online]. Retrieved from the Internet: <URL: https://www.thorlabs.com/>, (Accessed Jul. 19, 2021), 2 pgs.

Bosschaart, Nienke, et al., "A literature review and novel theoretical approach on the optical properties of whole blood", Lasers Med Sci, (2014), 453-479.

Dobrzanski, L A, et al., "Al2O3 antireflection coatings for silicon solar cells", Journal of Achievements in Materials and Manufacturing engineering, vol. 59, Issue 1, (Jul. 2013), 13-19.

Jacques, Steven, "Optical Absorption of Carbonized Tissue", [Online]. Retrieved from the Internet: <URL: https://omlc.org/spectra/carbon/>, (2018), 3 pgs.

Vinnichenko, Victoriya, et al., "Comparison of a novel high-power blue diode laser ($\lambda$=442 nm) with Ho:YAG ($\lambda$=2100 nm), Tm fiber ($\lambda$=1940 nm), and KTP ($\lambda$=532 nm) lasers for soft tissue ablation", Proc. SPIE 10468, Therapeutics and Diagnostics in Urology, [Online]. Retrieved from the Internet: <URL: https://www.researchgate.net/publication/323002187>, (Feb. 2018), 8 pgs.

Yaroslavsky, A, et al., "Optical properties of selected native and coagulated human brain tissues in vitro in the visible and near infrared spectral range", Phys. Med. Biol. 47, (2002), 2059-2073.

"U.S. Appl. No. 18/055,486, Final Office Action mailed Apr. 3, 2024", 8 pgs.

"U.S. Appl. No. 18/055,486, Response filed May 10, 2024 to Final Office Action mailed Apr. 3, 2024", 12 pgs.

"U.S. Appl. No. 18/055,486, Advisory Action mailed May 20, 2024", 3 pgs.

"Japanese Application Serial No. 2022-507462, Appeal of an Adverse Decision filed May 24, 2024", with English claims, 24 pgs.

"U.S. Appl. No. 18/055,486, Final Office Action mailed Jun. 24, 2024", 9 pgs.

"Chinese Application Serial No. 202080061567.3, Response filed Apr. 23, 2024", with English claims, 14 pgs.

"U.S. Appl. No. 18/055,486, Response filed Sep. 25, 2023 to Restriction Requirement mailed Jul. 24, 2023", 8 pgs.

"U.S. Appl. No. 18/055,486, Non Final Office Action mailed Oct. 16, 2023", 8 pgs.

"Chinese Application Serial No. 202080061567.3, Office Action mailed Oct. 24, 2023", W English Translation, 18 pgs.

"Japanese Application Serial No. 2022-507462, Response filed Nov. 9, 2023 to Office Action mailed Jul. 4, 2023", w english claims, 15 pgs.

U.S. Appl. No. 16/984,447 U.S. Pat. No. 11,523,865, filed Aug. 4, 2020, Target Identification With Optical Feedback Signal Splitter.

U.S. Appl. No. 17/376,958 U.S. Pat. No. 11,406,447, filed Jul. 15, 2021, Target Identification With Optical Feedback Signal Splitter.

U.S. Appl. No. 18/055,486, filed Nov. 15, 2022, Target Identification With Opitcal Feedback Signal Splitter.

"U.S. Appl. No. 18/055,486, Examiner Interview Summary mailed Jan. 12, 2024", 2 pgs.

"U.S. Appl. No. 18/055,486, Response filed Jan. 10, 2024 to Non Final Office Action mailed Oct. 16, 2023", 12 pgs.

"Chinese Application Serial No. 202080061567.3, Response filed Mar. 6, 2024 to Office Action mailed Oct. 24, 2023", W/English Claims, 16 pgs.

"Japanese Application Serial No. 2022-507462, Examiners Decision of Final Refusal mailed Jan. 30, 2024", w/ English Translation, 11 pgs.

"U.S. Appl. No. 18/055,486, Advisory Action mailed Jul. 16, 2024", 3 pgs.

"U.S. Appl. No. 18/055,486, Examiner Interview Summary mailed Jul. 8, 2024", 2 pgs.

"U.S. Appl. No. 18/055,486, Response filed Jul. 3, 2024 to Final Office Action mailed Jun. 24, 2024", 12 pgs.

"U.S. Appl. No. 18/055,486, Response filed Sep. 6, 2024 to Final Office Action dated Jun. 24, 2024 and Advisory Action mailed Jul. 16, 2024", 12 pgs.

\* cited by examiner

TARGET IDENTIFICATION WITH OPTICAL FEEDBACK SIGNAL SPLITTER

CLAIM OF PRIORITY

This application is a Continuation of U.S. patent application Ser. No. 18/055,486, filed Nov. 15, 2022, which is a Continuation of U.S. patent application Ser. No. 16/984,447, filed Aug. 4, 2020 and now issued as U.S. Pat. No. 11,523,865, which claims the benefit of priority under 35 U.S.C. § 119(e) of U.S. Provisional Patent Application Ser. No. 62/882,837, filed on Aug. 5, 2019, U.S. Provisional Patent Application Ser. No. 62/931,360, filed on Nov. 6, 2019, U.S. Provisional Patent Application Ser. No. 63/008,940, filed on Apr. 13, 2020, and U.S. Provisional Patent Application Ser. No. 63/018,262, filed on Apr. 30, 2020, which are herein incorporated by reference in their entireties.

FIELD OF THE DISCLOSURE

The documents relates generally to optical surgical system, and more particularly to techniques for target identification using an optical response signal sharing a pathway with another optical signal.

BACKGROUND OF THE DISCLOSURE

Laser or plasma systems have been used for delivering surgical laser energy to various target treatment areas such as soft or hard tissue. Examples of the laser therapy include ablation, coagulation, vaporization, fragmentation, etc. In lithotripsy applications, laser has been used to break down calculi structures in kidney, gallbladder, ureter, among other stone-forming regions, or to ablate large calculi into smaller fragments.

Endoscopes are typically used to provide access to an internal location of a subject such that a physician is provided with visual access. An endoscope is normally inserted into a patient's body, delivers light to a target (e.g., a target anatomy or object) being examined, and collects light reflected from the object. The reflected light carries information about the object being examined. Some endoscopes include a working channel through which the operator can perform suction or pass instruments such as brushes, biopsy needles or forceps, or perform minimally invasive surgery to remove unwanted tissue or foreign objects from the body of the patient.

In certain procedures employing electromagnetic energy, there is no way of identifying composition of a target while executing the procedure. For health-related procedures, it can be difficult to identify whether a target is soft or hard tissue in vivo. There are some surgical methods that can be used to extract tissue and then identify the composition of the tissue once it has been removed from the body, but tissue composition cannot be determined in vivo.

SUMMARY

Figure 1:
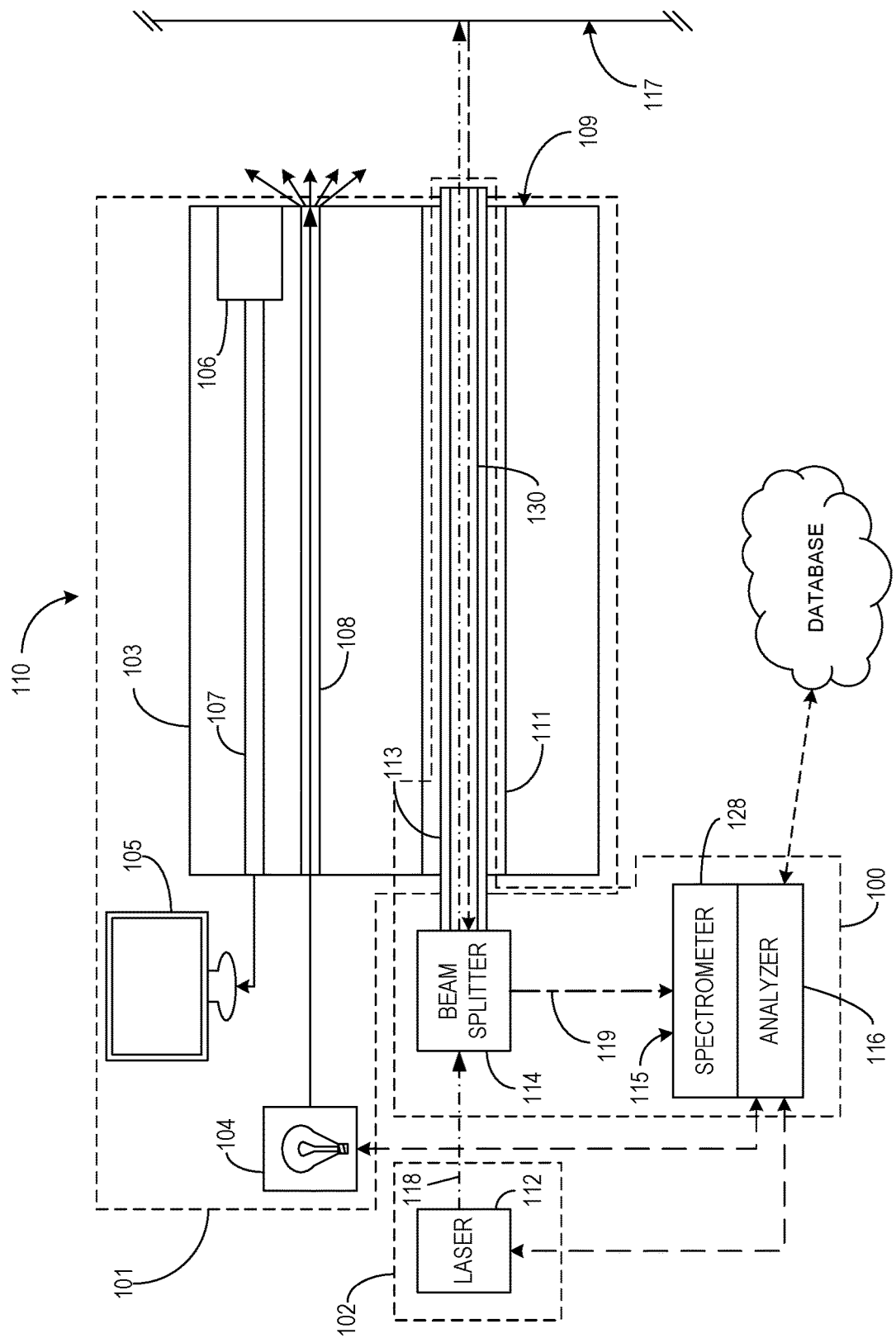
FIG. 1 illustrates generally an example target identification system within a surgical system such as an ablation system.

Techniques are provided for determining a composition of a target while performing a procedure to the target. For ease of understanding, the techniques are described in terms of health-related procedures but are not so limited. Techniques are provided for determining a composition of tissue in vivo (internal to a patient) such as while conducting a medical procedure at or near the tissue. As an example, for ablation of obstructive tissue such as renal calculi, tissue composition information can assist in executing the procedure more efficiently and effectively. The present techniques can include or use a system comprising a viewing instrument including a lumen, a working instrument, a light source, a beam splitter, and a laser light source. The viewing instrument can include an endoscope or a laparoscope, such as can define a proximal end and a distal end. The working instrument can include a working probe, such as can extend through the lumen of the viewing instrument. The light source can illuminate an area beyond the distal end of the viewing instrument, such as by providing illumination via an optical path of the viewing instrument. The beam splitter can be located at or coupled to a proximal end of the optical path of the working instrument. The laser light source can be coupled to the beam splitter and can generate a laser beam. The laser beam can pass from a proximal end of the working instrument to a distal end of the working instrument, such as via the optical path of the working instrument. The optical path of the working instrument can optionally pass an optical response signal received from the area beyond the distal end, such as for communication from the distal end of the working instrument to the beam splitter located at the proximal end of the working instrument.

Example 1 is a target identification system comprising: a probe having a first end and a second end, the second end configured to locate adjacent an anatomical target, the probe configured to define an optical path, the optical path configured to simultaneously pass a first optical signal and a second optical signal representative of the anatomical target; and a beam splitter comprising: a first port coupled to the first end of the probe; a second port configured to align with the optical path and configured to pass the first optical signal; and wherein the beam splitter is configured to redirect the second optical signal representative of the anatomical target from the optical path and from the first optical signal.

In Example 2, the subject matter of Example 1 optionally includes a spectrometer optically coupled to the beam splitter, the spectrometer configured to receive from the beam splitter the second optical signal representative of the anatomical target and to provide spectral measurements representative of the anatomical target.

In Example 3, the subject matter of Example 2 optionally includes a feedback analyzer configured to receive the spectral measurements and to generate a composition profile of the target.

In Example 4, the subject matter of any one or more of Examples 2-3 optionally includes, wherein the beam splitter includes: a focusing lens; an optical sensor; and wherein the focusing lens includes a wavelength sensitive layer, the wavelength sensitive layer configured to pass the first optical signal along the optical path and to redirect the second optical signal toward the optical sensor.

In Example 5, the subject matter of Example 4 optionally includes, wherein the optical sensor is configured to couple to the spectrometer and to convert the second optical signal to one or more electrical signals.

In Example 6, the subject matter of any one or more of Examples 2-5 optionally includes, wherein the beam splitter includes: a focusing lens having a wavelength sensitive layer, the wavelength sensitive layer configured to pass the first optical signal along the optical path and to redirect the second optical signal; a third optical port coupled to spectroscopic system; and an integrating sphere configured to further redirect the second optical signal to the third optical port.

In Example 7, the subject matter of any one or more of Examples 2-6 optionally includes, wherein the beam splitter includes: a third optical port; and a dichroic mirror configured to pass the first optical signal from the first port to the second port, and to redirect the second optical signal to a third optical port.

Example 8 is a surgical system comprising: a viewing instrument including a lumen, the viewing instrument and the lumen defining a proximal end and a distal end, the viewing instrument comprising a light source configured to illuminate an anatomical target via an optical path of the viewing instrument; and a target identification system comprising: a working probe configured to extend through the lumen; a beam splitter coupled to a proximal end of the working probe, the beam splitter configured to split an optical response signal indicative of the target from the optical path; and a spectrometer optically coupled to the beam splitter, the spectrometer configured to receive from the beam splitter at least a representation of the optical response signal and provide spectral measurements representative of the anatomical target.

In Example 9, the subject matter of Example 8 optionally includes, wherein the beam splitter includes: a first port coupled to the proximal end of the probe; and a second port configured to align with the optical path and configured to pass a second optical signal.

In Example 10, the subject matter of Example 9 optionally includes, wherein the beam splitter includes: a focusing lens; an optical sensor; and wherein the focusing lens includes a wavelength sensitive layer, the wavelength sensitive layer configured to pass the second optical signal along the optical path and to redirect the optical response signal toward the optical sensor.

In Example 11, the subject matter of Example 10 optionally includes, wherein the optical sensor is configured to couple to the spectrometer and to convert the optical response signal to one or more electrical signals.

In Example 12, the subject matter of any one or more of Examples 9-11 optionally includes, wherein the beam splitter includes: a focusing lens in a path of the optical path, the focusing lens including a wavelength sensitive layer, the wavelength sensitive layer configured to pass the second optical signal along the optical path and to redirect the optical response signal to provide a redirected optical response signal; a third optical port coupled to spectrometer; and an integrating sphere configured to reflect the redirected optical response signal to the third optical port.

In Example 13, the subject matter of any one or more of Examples 9-12 optionally includes, wherein the beam splitter includes: a third optical port coupled to the spectrometer; and a dichroic mirror configured to pass the second optical signal along the optical path, and to reflect the optical response signal to the third optical port.

In Example 14, the subject matter of any one or more of Examples 8-13 optionally includes, wherein the target identification system includes a feedback analyzer configured to receive spectral information and to generate a composition profile of the target.

In Example 15, the subject matter of Example 14 optionally includes a procedure instrument configured to utilize the working probe contemporaneously with the optical response signal transiting the optical path; and wherein the feedback analyzer is configured to provide control signals to the procedure instrument based on the composition profile.

In Example 16, the subject matter of Example 15 optionally includes, wherein the procedure instrument includes a laser configured to generate a laser beam, the laser beam configure to transit the optical path from the beam splitter to the distal end of the probe contemporaneously with the optical response signal transiting the optical path.

Example 17 is a laser surgery system comprising: a laser system configured to generate a laser beam operable to ablate a target within a patient's body; an optical probe comprising: an optical fiber configured to transmit the laser beam to the target and to transmit target light from the target; and a beam splitter configured to pass the laser beam from the laser system to the optical fiber and to receive the target light and split the target light from the laser beam; a spectrometer optically coupled to the beam splitter, the spectrometer configured to receive the target light split from the laser beam and to generate spectral information of the target light; and feedback circuitry configured to receive the spectral information and determine composition information of the target.

In Example 18, the subject matter of Example 17 optionally includes, wherein the laser system is configured to receive the composition information and to adjust the laser beam responsive to the composition information.

Example 19 is a method comprising: extending a working instrument via a first lumen of a viewing instrument; illuminating an anatomical target via an optical path of the viewing instrument; passing an optical response signal of the anatomical target via an optical path of the working instrument; and splitting the optical response signal from the optical path of the working instrument.

In Example 20, the subject matter of Example 19 optionally includes, wherein the viewing instrument is an endoscope.

In Example 21, the subject matter of any one or more of Examples 19-20 optionally includes, wherein the viewing instrument is a laparoscope.

In Example 22, the subject matter of any one or more of Examples 19-21 optionally include passing the optical response signal to a spectroscopy system.

In Example 23, the subject matter of any one or more of Examples 19-22 optionally include passing a second optical signal via the optical path of the working instrument at while passing the optical response signal.

In Example 24, the subject matter of Example 23 optionally includes, wherein the second optical signal is a laser beam configured to ablate the anatomical target.

In Example 25, the subject matter of Example 24 optionally includes, wherein passing the optical response signal to a spectroscopy system includes splitting the optical response from the optical path of the working instrument to a third optical path.

In Example 26, the subject matter of Example 25 optionally includes, wherein passing the laser beam includes merging an optical path extending from the laser with the optical path of the working instrument.

In Example 27, the subject matter of Example 26 optionally includes, wherein merging an optical path extending from the laser includes passing the laser beam through a dichroic mirror; and wherein splitting the optical response from the optical path of the working instrument includes reflecting the optical response a surface of the dichroic mirror.

This section is intended to provide an overview of subject matter of the present patent application. It is not intended to provide an exclusive or exhaustive explanation of the invention. The detailed description is included to provide further information about the present patent application.

DETAILED DESCRIPTION

Identifying the composition of tissue in vivo via an endoscope or laparoscope has numerous applications. For example, if the composition of a renal calculus could be determined a priori, the treatment method could be based at least in part on the composition of the stone. For example, when using a laser to break-up or "dust" a stone, if it were known a priori that the stone had a hard composition, then the laser settings could be adjusted to settings that perform better on a hard kidney stone.

Also, techniques that require the removal of a tissue sample to identify the composition cannot monitor the composition of the tissue on an ongoing basis through all or a portion of entire procedure. The present techniques can allow measurement and analysis of the composition of an anatomical target, or target tissue, at the tip of the endoscope or laparoscope. These techniques can provide more information during a health related procedure, such as a surgical or diagnostic procedure, to better adapt a treatment method during the procedure. For example, if a procedure involves breaking a renal calculus into tiny pieces, e.g., "dusting" the renal calculi, that has a hard surface, but a soft core, the continuous or other ongoing monitoring of the target tissue composition via the endoscope or laparoscope can allow adjustment of, for example, the settings of the instrument doing the "dusting" during the procedure, such as laser settings for a laser ablation instrument. The identification of the target tissue can allow for first providing settings that perform better on the hard surface of the stone to then providing settings that perform better on the soft core of the stone.

FIG. 1 illustrates generally an example target identification system 100 within a surgical system 110 such as an ablation system. The surgical system 110 can include visualization equipment such as an endoscope 101, the target identification system 100, and primary medical equipment such as a laser ablation system 102. The endoscope 101 can include an endoscope probe 103, a laser or other light source 104 and a display assembly 105. The endoscope probe 103 can include a camera 106, one or more optical signal communication pathway 107, 108, and at least one working lumen 111. A distal portion of the endoscope probe 103 can be inserted within a patient's body. The light source 104, one or more optical transmission media 107, 108, and display assembly 105 can allow an end-user, such as a physician or surgeon or robotic device, to illuminate and observe an internal area of the patient's body at or near the distal end 109 of the endoscope probe 103. For example, the light source 104 can illuminate the area at or beyond the distal end 109 of the endoscope probe 103 via a first optical transmission media 108, and a second optical transmission media 107 can communicate image signal information from the camera at the distal end 109 of the endoscope probe 103 to signal processing circuitry at the display 105 for displaying an image of the area at or beyond the distal end 109 of the endoscope probe 103. In some examples, the second optical or electrical transmission media 107 can include one or more components such as one or more optical fibers and the display 105 can include an eyepiece for the end-user to observe the area at or beyond the distal end 109 of the endoscope probe 103. In certain examples, the second optical transmission media 107 can couple viewing image signal information from the camera 106 to an electronic display 105 such as for the end-user to observe the area at or beyond the distal end 109 of the endoscope probe 103. In some examples, the camera 106 can be located at or near the proximal end of the endoscope probe 103, such as near the display 105, and one or more optical fibers can form the second optical transmission media 107 to transmit the image information from the distal end 109 of endoscope probe 103 to the camera 106. In some examples, the camera 106 can be located at the distal end 109 of the endoscope probe 103, and image information can be transmitted to the display 105 via electrical conductors forming the second optical transmission media 107 integrated with the endoscope probe 103.

The working lumen 111 can further allow the end-user to insert and extract a portion of the primary medical instrument such as one or more surgical tools for operating about the targeted internal region of the patient's body being visualized using the endoscope probe 103. For example, for a surgical ablation system 102, the primary medical instrument can include a working probe 113 and a laser 112 to allow ablation of tissue at or near the distal end 109 of the endoscope probe 103. In such a system, for either endoscopic or laparoscopic procedures, a laser beam 118 can pass energy through the working lumen 111 to effectively treat hard and soft tissue. In certain examples, the laser system 102 can produce a laser output beam 118 in a wide wavelength range from ultraviolet (UV) to infrared (IR) (e.g., 200 nm to 10000 nm). Some lasers can produce an output in a wavelength range that can be highly absorbed by soft or hard tissue, for example 1900-3000 nm for water absorption or 400-520 nm for oxy-hemoglobin and/or deoxy-hemoglobin absorption.

The working probe 113 may also be a part of the target identification system 100. The target identification system 100 can include the working probe 113, an optical beam splitter 114, and a spectroscopy system 115. The spectroscopy system 115 can include a spectrometer 128 and an optional feedback analyzer 116. The target identification system 100 can use image response information such as content of electromagnetic emissions, either reflected or radiated from a target, to assist in determining a material or composition of the target, such as target tissue. Such electromagnetic emissions can include, but is not limited to, light visible to the human eye, florescent emissions, ultraviolet light, infrared light, or combinations thereof.

In certain examples, such image response information can be used to more efficiently execute a procedure. In an example, light from the light source 104 can reflect off the target tissue 117 or can cause the target tissue to emit optical information, such as by florescence, for example. Such optical information is referred to herein as image response information or optical response information conveyed for example via an optical response signal 119. The spectrometer 128 or spectroscopy system 115 can be optically coupled to the beam splitter 114, and can provide spectral measurements from the optical response signal 119. Such spectral measurements can be used to determine characteristics of the target such a materials, hardness, etc. which, in turn, can be used to guide the procedure. Such guidance may result in selecting a different tool, adjusting a tool (e.g. laser setting) or combinations thereof to more efficiently proceed with the procedure.

Spectroscopy/spectrometry techniques can be used to identify materials or structures via the spectrum reflected, transmitted, emitted, absorbed, or not absorbed by a target surface. Optical spectroscopy can provide timely analysis of organic and inorganic materials. For ablation, optical spectroscopy can help provide several advantages, such as including, but not limited to, integration with fiber laser ablation techniques, nondestructive methods of material chemical composition analyses, real-time or near real-time composition estimates or profiles, and applicability for analyses of different types of biological materials: hard and soft tissue, stones, and others. Spectroscopic techniques can be used alone or in combination to analyze hard or soft tissue chemical composition and create digital spectral data. In some examples, one or more types of spectroscopy, including but not limited to, color, ultra-violet, deep ultra-violet, visual light, near-infrared, and florescent spectroscopy, can be used with the endoscope 103 to identify the composition of target tissue 117. In an example, the spectroscopy system 112 can initiate and control the light source 104 illuminating the target tissue via, for example, the first optical transmission media 108 of the endoscope probe 103, can receive optical response signal either reflected from or generated at the target tissue 117 such as via an optical transmission media of the working probe 113, and can generate spectral data based on the optical response signal 119. In certain examples, the light source 103 can include, but is not limited to, a visible light source, an infrared light source, an ultra-violet light source, a fluorescent light source, or a combination thereof.

The feedback analyzer 116 can receive a spectroscopic response signal delivered from the spectrometer 128, can estimate a composition or compositions profile of the materials represented by the spectral data, and can display such estimates or provide one or more control signals for controlling the primary surgical instrument 102. The composition or structure information can be useful to help provide feedback that can be used for more efficiently performing the surgical procedure. For example, the feedback analyzer 116 can compare the spectroscopic response signal with an available database library of tissue composition data. The feedback analyzer 116 can estimate target material composition based on the spectroscopic response signal and suggest a configuration for the primary surgical instrument 102 to achieve effective tissue treatment for the identified tissue composition. In certain examples, the feedback analyzer 116 can provide one or more control signals or control data to adjust one or more parameter settings of the primary surgical instrument 102. In a laser ablation example, the feedback analyzer 116 or an intermediate device, can program laser settings automatically based on the target material composition estimate. In some examples, adjustment of the laser settings can be limited or constrained to be within a set individual or multivariate safe operating range such as based on a setting selected by the end-user at the start of the procedure.

In certain examples, the spectroscopy system 115 can optionally communicate with a database 129. In some examples, the database 129 can be a repository for measurements and other information associated with a procedure. In some examples, as the database collects more information, the spectroscopy system 102 or a portion thereof, such as the feedback analyzer 116, can interact with information of the database 129 to determine, for example, the most efficient application of the laser system 112 based on spectroscopic information collected or analyzed during the procedure and compare with the historical information available in the database 129. In certain examples, the database may be able to provide temporal recipe for configuration of the primary surgical instrument 102 as the spectroscopic information of a procedure is collected and analyzed. In certain examples, the database 129 can include an internet-based or a cloud-based database and may include applications designed for interacting with a feedback analyzer 116 or some other portion of the spectroscopy system 102 to assist in executing an efficient surgical procedure based on historical procedure information and adaptive to the specific spectroscopic information collected during the procedure.

For example, for a laser ablation system, the laser settings that can be part of a recipe for configuration of the primary surgical instrument 102 can include, but are not limited to, laser operation mode (e.g., pulse or continuous wave), power, energy, frequency, pulse shape, pulse profile, or one or more combinations thereof. In certain examples, the laser system 112 can operate in an automatic mode or a semi-automatic mode among other modes. In automatic mode, the laser settings can be automatically controlled based on the target material composition estimate. In semi-automatic mode, the laser settings can be adjusted based on the target material composition estimate after receiving some confirmatory indication of operator approval for making the setting change. The combination of the laser system 112, spectroscopy system 115, and the feedback analyzer 116 can be used in an ongoing intraoperative feedback mode such as to continuously or recurrently identify the composition of target tissue 117 through the working probe 113 and update the laser settings during or throughout a procedure. It is understood that other surgical techniques other than laser-based surgical techniques as discussed herein are possible to use with the target identification system 100 without departing from the scope of the present subject matter In certain examples, a single optical transmission media of the working probe 113 of the target identification system 100 can be used to transport a first type of electromagnetic emission or beam to or from the target tissue 117 at the distal end 109 of the working probe 113 and can also be used to transport an optical response signal from the distal end 109 of the working probe 113 to the spectroscopy system 115. The optical splitter 114 can be used to merge multiple optical pathways into a single optical pathway or to separate optical information from a common optical pathway to one or more separate optical pathways. The optical splitter 114 can make use of a wavelength sensitive coating such an anti-reflective coating or material or a dichroic coating or material or a combination thereof. Suitable material for anti-reflection coatings can include $SiO_2$ (refractive index between about 1.4 and about 1.5), SiO (refractive index between about 1.8 and about 1.9), $Si_3N_4$ (refractive index of about 1.9), $TiO_2$ (refractive index of about 2.3), $Ta_2O_5$ (refractive index between about 2.1 and about 2.3), $MgF_2$ (refractive index between about 1.4 and about 1.5), $BaF_2$ (refractive index of about 1.47), and others.

Figure 2:
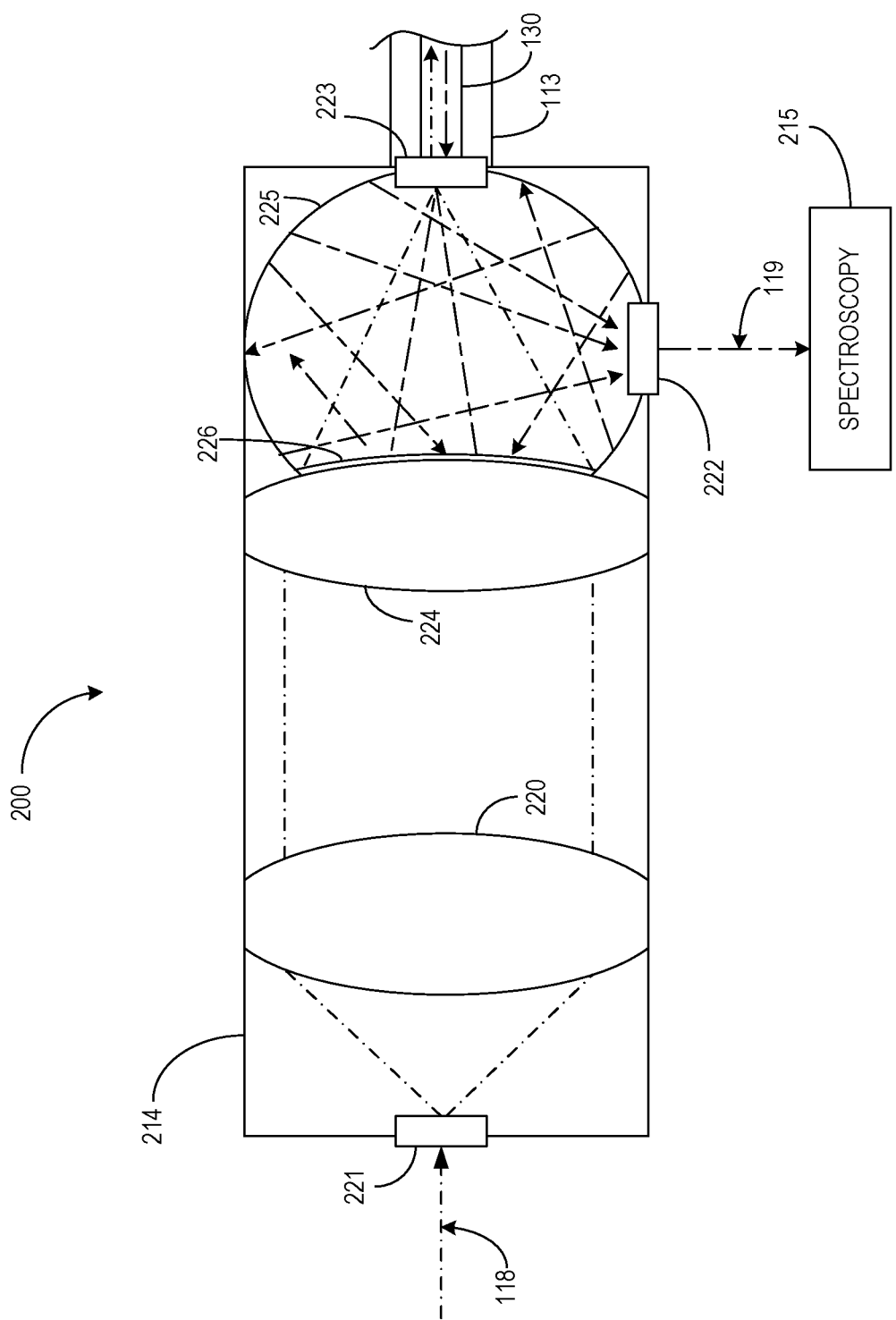
FIG. 2 illustrates generally a detailed example of a target identification system.

FIG. 2 illustrates generally a detailed example of a target identification system 200. The target identification system 200 can include a beam splitter 214, a probe 113, and a spectroscopy system 215. The beam splitter 214 can include at least three ports 221, 222, 223, a collimation lens 220, a focus lens 224, and an integrating sphere 225. The three ports 221, 222, 223 can include a first port 221 for a first optical pathway, a second port 222 for a feedback optical pathway to the spectroscopy system, and a third port 223 for a common optical pathway 130 for transmitting a first optical signal, such as a laser beam 118, and an optical response signal 119 between the beam splitter 214 and the distal end of the probe 113. As an example, laser energy can be coupled from the first port 221 to the third port 223 such as via the collimation lens 220 and the focus lens 224, and the optical response signal 119 can be coupled from the third port 223 to the second port 222 such as via a combination of the focus lens 224 and the integrating sphere 225. The focus lens 224 can include a wavelength sensitive material or coating 226, such as an AR material, that can be transparent or anti-reflective to the wavelength of the laser, but highly reflective to wavelengths of interest of the optical response signal 119. As such, much if not all of the laser energy can be passed from the first port 221 to the third port 223. The optical response signal 119 can be received via the third port 223 and reflected back or redirected into the integrating sphere 225 such as by a coated surface of the focus lens 224. The interior surfaces of the integrating sphere 225 can continue to redirect the optical response signal 119 around until the optical response signal 119 exits the integrating sphere 225 via the second port 222. Upon exiting the integrating sphere 225 via the second port 222, the optical response signal 119 can be transmitted to the spectroscopy system.

Figure 3:
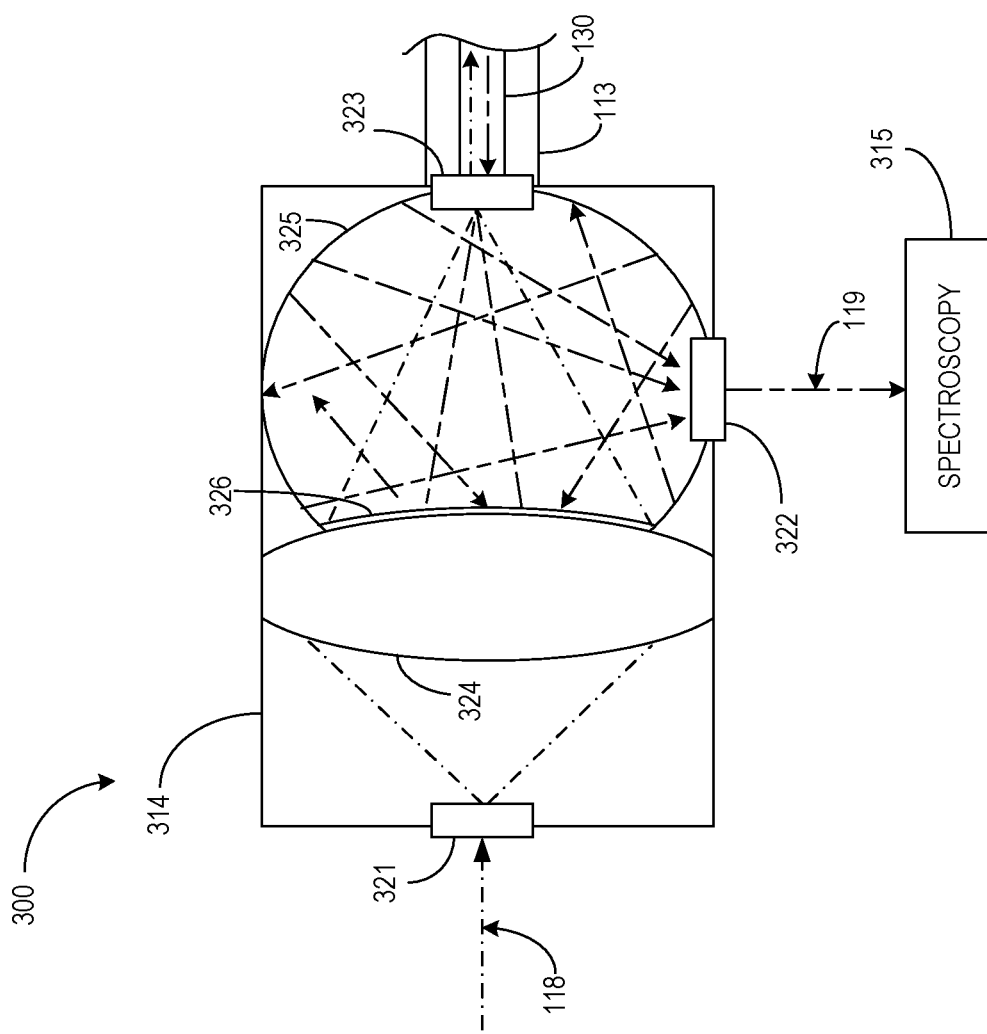
FIG. 3 illustrates generally an example of a beam splitter within an example target identification system.

FIG. 3 illustrates generally a detailed example of a target identification system 300. The target identification system 300 can include a beam splitter 314, a probe 113, and a spectroscopy system 315. The beam splitter 314 can include at least three ports 321, 322, 323, a focusing lens 324, and an integrating sphere 325. The three ports 321, 322, 323 can include a first port 321 for a laser optical pathway coupled to the laser, a second port 322 for a feedback optical pathway to the spectroscopy system, and a third port 323 for a common optical pathway 130 for transmitting both the laser and the optical response signal 119 between the beam splitter 314 and the distal end of the working probe 113. Unlike the beam splitter of FIG. 2, the focus lens 324 can be designed to perform both the collimating function of the laser light and the focusing function of the laser light to the third port 323. In operation, the laser energy is coupled from the first port 321 to the third port 323 via the focusing lens 324 and the optical response signal 119 is coupled from the third port 323 to the second port 322 via a combination of the focusing lens 324 and the integrating sphere 325. In certain examples, the focusing lens 324 can include a wavelength sensitive material or coating 326, such as an AR material, that is transparent or anti-reflective to the wavelength of the laser, but highly reflective to the wavelengths of the optical response signal 119. As such, much of the laser energy is passed from the first port 321 to the third port 323 while the optical response signal 119 received from the third port 323 is reflected into the integrating sphere 325. The integrating sphere 325 can continue to reflect the optical response signal 119 around until the image information exits the integrating sphere 325 via the second port 322. Upon exiting the integrating sphere 325 via the second port 322, the optical response signal 119 can be transmitted to the spectroscopy system.

Figure 4:
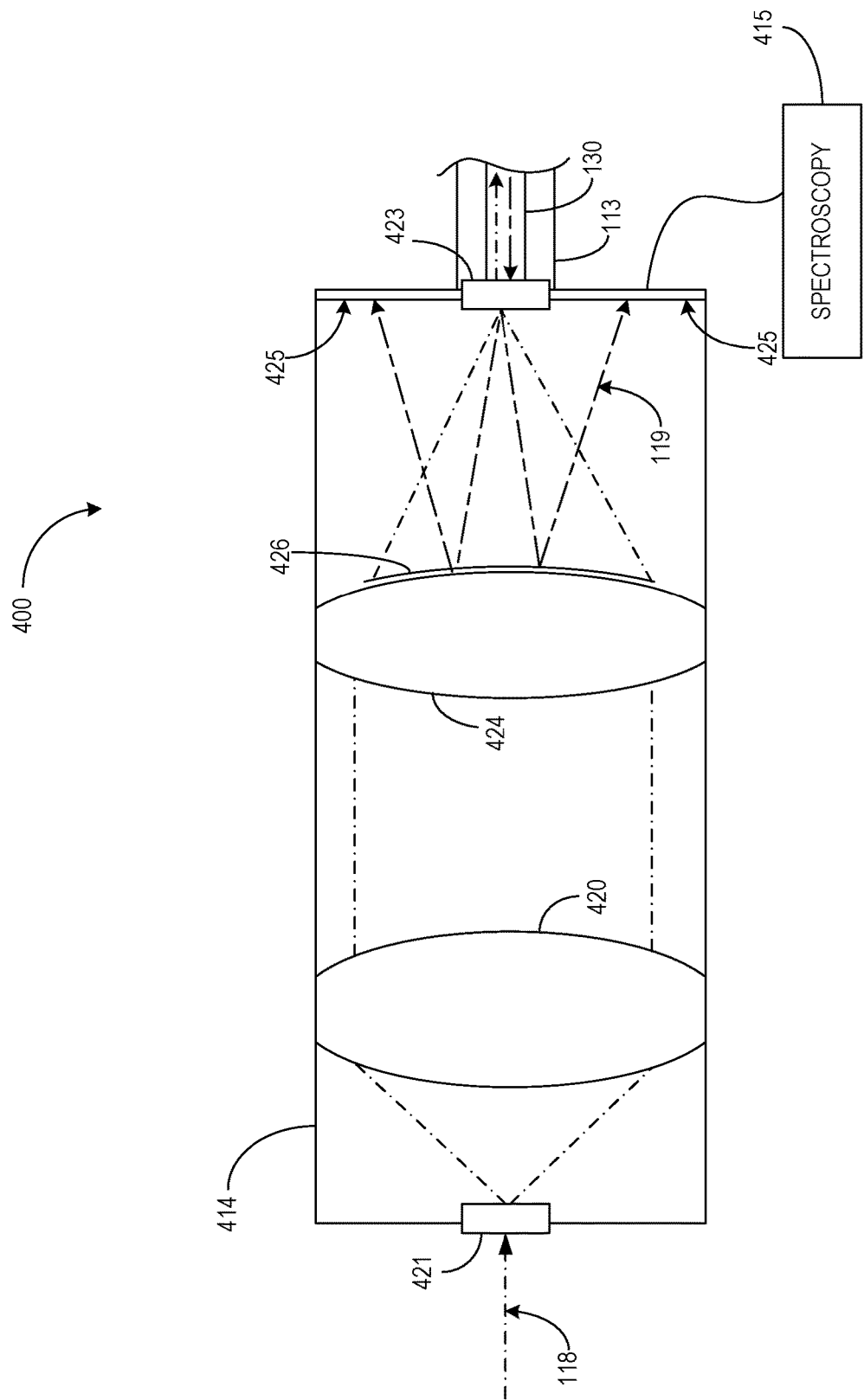
FIG. 4 illustrates generally a detailed example of a beam splitter within an example target identification system.

FIG. 4 illustrates generally a detailed example of a target identification system 400. The target identification system 400 can include a beam splitter 414, a probe 113, and a spectroscopy system 415. The beam splitter 414 can include two ports 421, 423, a collimation lens 420, a focus lens 424, and an optical sensor 425. The two ports 421, 423 can include a first port 421 for a laser optical pathway coupled to the laser, and a second port 423 for a common optical pathway 130 for transmitting both the laser and the optical response signal 119 between the beam splitter 414 and the distal end of the working probe. In operation, the laser energy is coupled from the first port 421 to the third port 423 via the collimation lens 420 and the focus lens 424. The focus lens 424 can include a wavelength sensitive material or coating 426, such as an AR material, that is transparent or anti-reflective to the wavelength of the laser, but highly reflective to wavelengths of interest of the optical response signal 119. As such, much if not all of the laser energy is passed from the first port 421 to the third port 423. The optical response signal 119 can be received via the third port 423 and reflected back or redirected to the optical sensor 425. In the examples discussed above, the spectroscopy system typically can include an optical sensor for receiving the optical response signal 119. In the beam splitter 414 of FIG. 4, the optical sensor 425 for receiving the optical response signal 119 can be part of the beam splitter 414 and can form at least part of the optical pathway or optical transmission media for the optical response signal 119.

Figure 5:
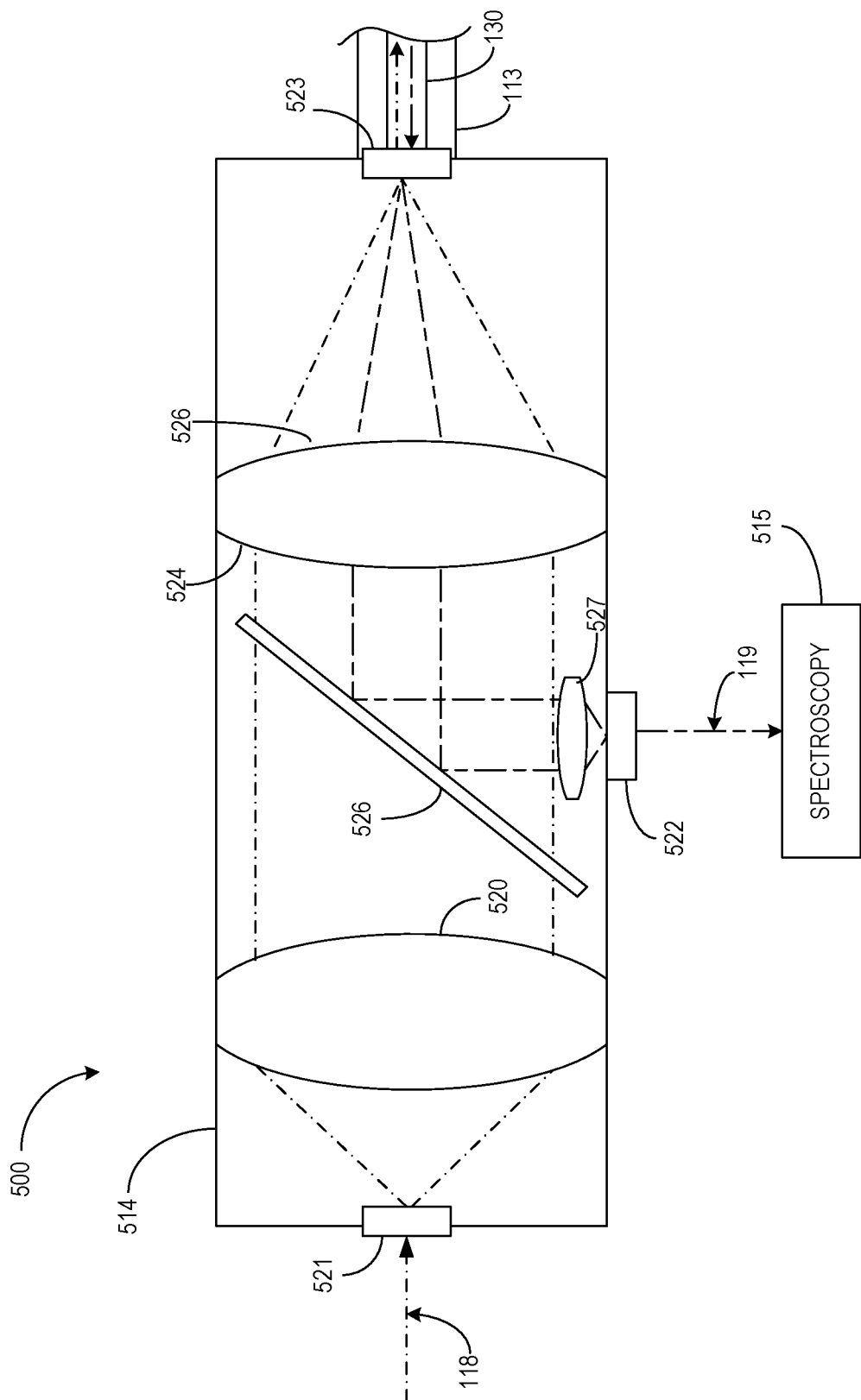
FIG. 5 illustrates generally a detailed example of a beam splitter within an example target identification system.

FIG. 5 illustrates generally a detailed example of a target identification system 500. The target identification system 500 can include a beam splitter 514, a probe 113, and a spectroscopy system 515. The beam splitter 514 can include at least three ports 521, 522, 523, a collimation lens 520, a first focus lens 524, and a dichroic mirror 526. In some examples, the beam splitter can include a second optional focusing lens 527. The three ports 521, 522, 523 can include a first port 521 for a laser optical pathway coupled to the laser, a second port 522 for a feedback optical pathway to the spectroscopy system, and a third port 523 for a common optical pathway 130 for transmitting both the laser and the optical response signal 119 between the beam splitter 514 and the distal end of the working probe. In operation, the laser energy is coupled from the first port 521 to the third port 523 via the collimation lens 520 and the first focus lens 524, and the optical response signal 119 is coupled from the third port 523 to the second port 522 via a combination of the focus lens 524 and the dichroic mirror 526. The dichroic mirror 526 allows light of a certain wavelength to pass through, while light of other wavelengths is reflected. In certain examples, such as in FIG. 5, such other wavelengths can include wavelengths of the optical response signal 119. In certain examples, the dichroic mirror 526 is fabricated to pass wavelengths associated with the laser energy and to reflect wavelengths associated with the optical response signal 119. As such, the dichroic mirror 526 can extract the optical response signal 119 from the common optical pathway 130 of that also includes the laser energy and divert the optical response signal 119 to the spectroscopy system via the second port 522 of the beam splitter 514. In certain examples, the focus lens 524 can include a wavelength sensitive material or coating 526, such as an AR material, that is transparent or anti-reflective to the wavelength of the laser, such that much if not all of the laser energy is passed from the first port 521 to the third port 523.

Figure 6:
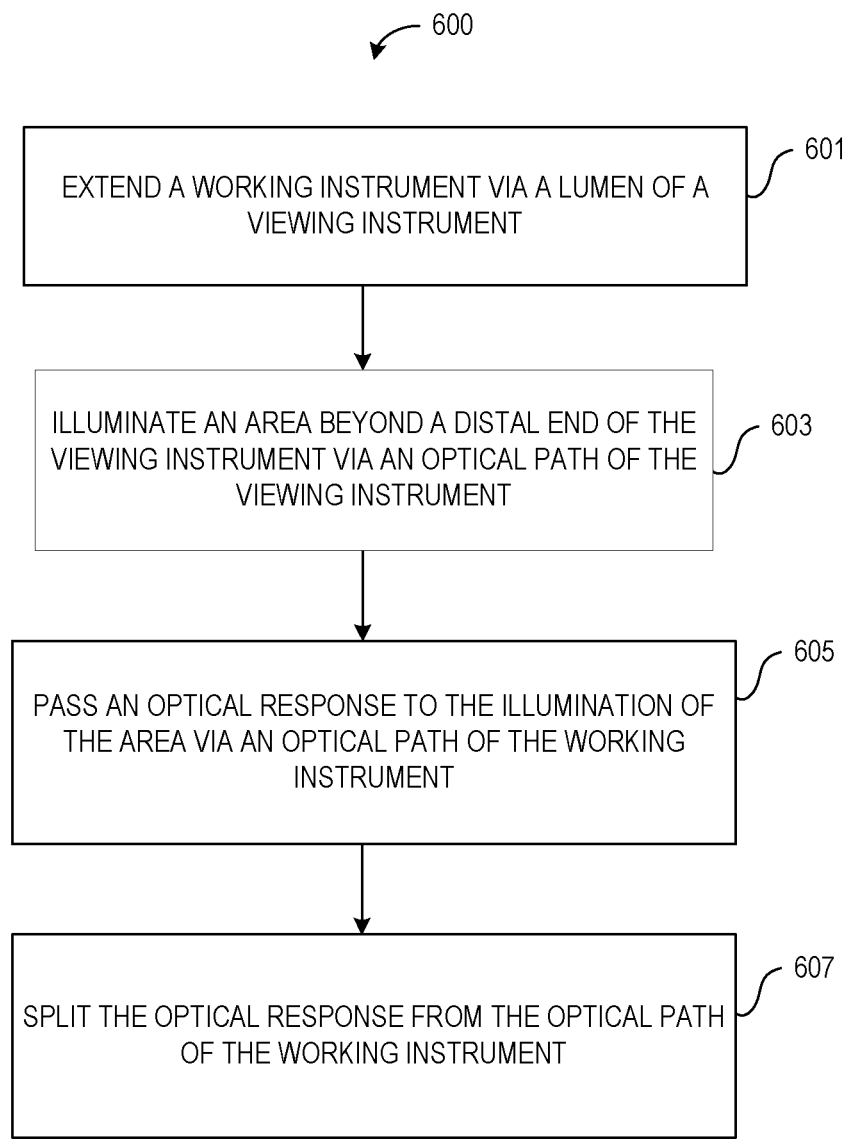
FIG. 6 illustrates generally an example of a method of operating an ablation system.

FIG. 6 illustrates generally an example of a method of operating an ablation system. At 601, a working instrument can be extended through a first lumen of a viewing instrument such as an endoscope. At 603, an area beyond a distal end of the viewing instrument can be illuminated via an optical path of the viewing instrument. A light source (e.g., FIG. 1, 104) can be located at a proximal or distal end of the viewing instrument. The light source can be a visible light source, an infrared light source, an ultraviolet light source, a fluorescent light source, or a combination thereof. At 605, in response to illumination of the area, optical response information, can be received, via an optical path of the working instrument, at a proximal end of the working instrument. The optical response information can include light reflected from target tissue in the area at the distal end of the endoscope. In certain examples, the optical response information can include light emitted from or generated from the target tissue in the area at the distal end of the endoscope. At 607, the optical response signal can be separated from the optical path of the working instrument such as by a beam splitter as discussed above. In certain examples, a second optical signal can be transmitted via the optical path of the working at the same time the optical response signal is being transmitted and separated or split from the optical path of the working instrument. As an example, the second optical signal can be a laser beam. For example, a laser beam can be passed between the proximal end of the working instrument and the area at the distal end via the optical path of the working instrument. Thus, the single optical path of the working instrument can be an optical transmission medium for simultaneous transmission of both the laser beam and the optical response information.

The optical response information can be used to detect the structure and composition of the target tissue. For example, the optical response information can be provided to a spectroscopy system. The spectroscopy system can include a spectrometer and a spectral analyzer. The spectrometer can provide spectral measurements of the optical response information. The spectral analyzer can compare the spectral measurements to one or more samples of expected compositions. The spectral analyzer can base an estimate the composition of the target tissue. In some examples, and end-user of the ablation system can adjust an operating parameter of the laser to more effectively treat the patent. For example, the composition estimate provided by the spectral analyzer can indicate that the target tissue currently being treated is harder or softer than prior-treated tissue. Such information can allow the end-user to adjust, for example, an intensity of the laser to more effectively ablate the harder or softer target tissue. In some examples, the spectral analyzer can automatically or semi-automatically adjust operating parameters of the laser or the light source in response to a composition estimate.

Figure 7:
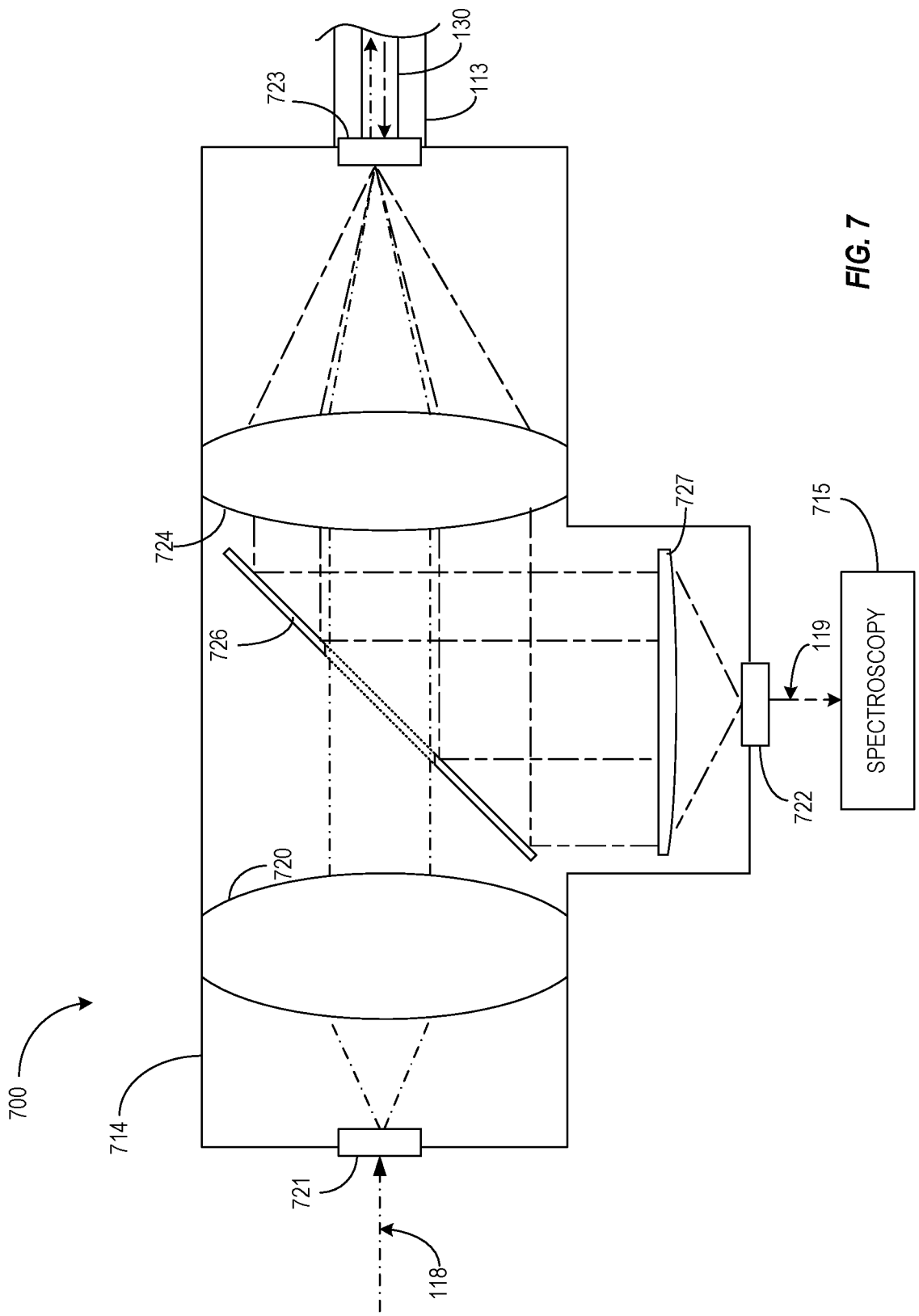
FIG. 7 illustrates generally an example of a beam splitter within an example target identification system.

FIG. 7 illustrates generally a detailed view of an example of a target identification system 700. The target identification system 700 can include a beam splitter 714, a working probe 113, and a spectroscopy system 715 optically coupled to the beam splitter 714. The beam splitter 714 can include at least three ports 721, 722, 723, a collimation lens 720, a first focus lens 724, and a reflector 726. The reflector 726 can be glass and may or may not have a coating. The reflector 726 can include an opening to allow laser light from a laser beam 118 to pass. In some examples, the beam splitter 714 can include a second optional focusing lens 727. The three ports 721, 722, 723 can include a first port 721 for a laser optical pathway coupled to the laser, a second port 722 for a feedback optical pathway to the spectroscopy system, and a third port 723 for a common optical pathway 130 for transmitting both the laser and the optical response signal 119 between the beam splitter 714 and the distal end of the working probe 113. In operation, the laser energy is coupled from the first port 721 to the third port 723 via the collimation lens 720, the opening in the reflector and the first focus lens 724. The optical response signal 119 can be coupled from the third port 723 to the second port 722 via a combination of the focus lens 724 and the reflector 726. In certain examples, the diameter and numerical aperture of the optical pathway at the third port 723 can be larger than the diameter and numerical aperture of the optical pathway providing the laser beam at the first port 721. The size relationship of the optical ports and numerical aperture can allow the optical response through the beam splitter to be expanded farther than the optical signal of the laser beam 118. As such, more light from the optical response can be collected without affecting the path of the laser beam compared to a path of the optical response that has less expansion.

Figure 8:
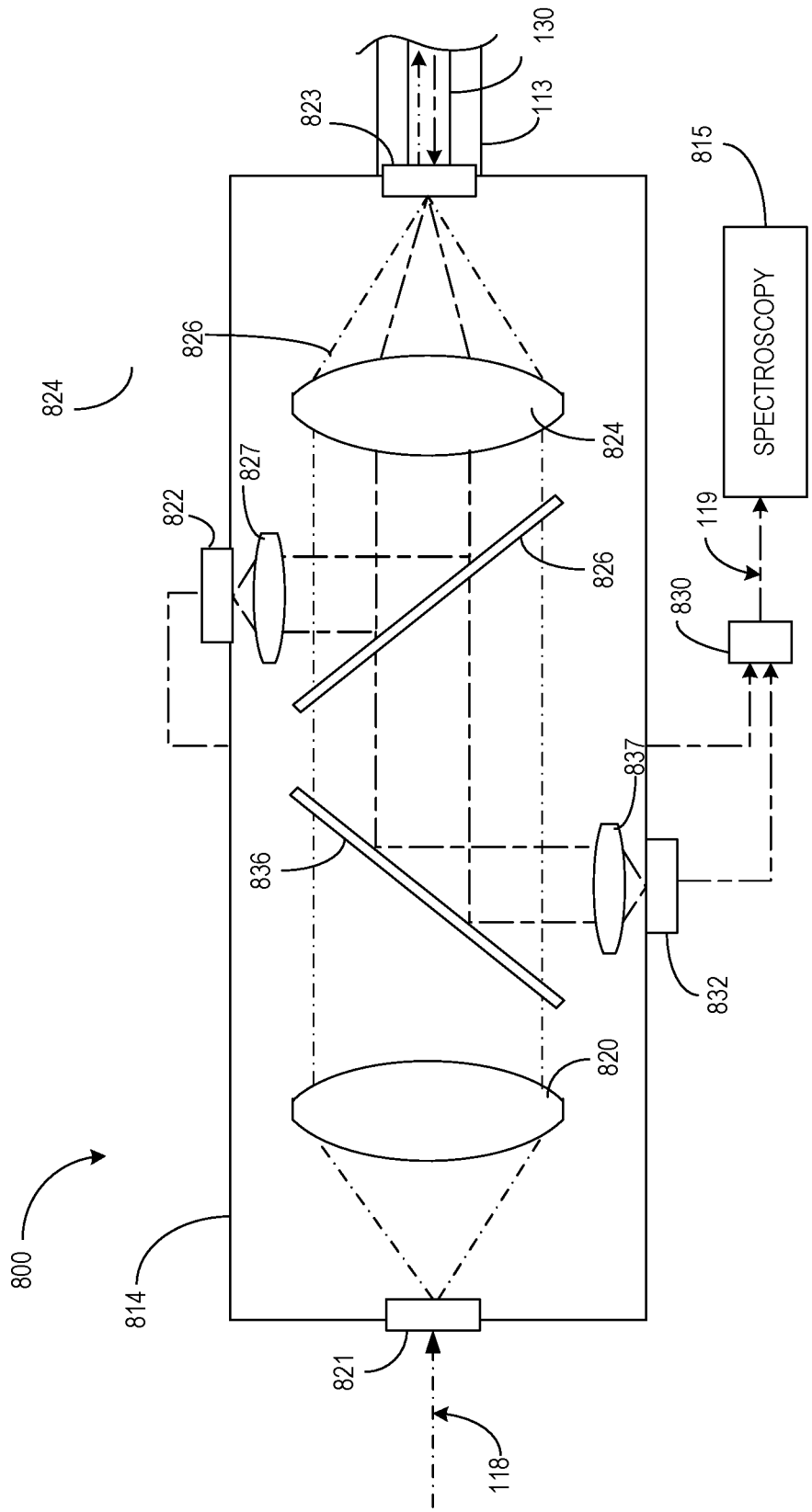
FIG. 8 illustrates generally an example of a beam splitter within an example target identification system.

FIG. 8 illustrates generally a detailed view of an example of a target identification system 800. The target identification system 800 can include a beam splitter 814, a working probe 113, and a spectroscopy system 815. The beam splitter 814 can include at least three ports 821, 822, 823, 832 a collimation lens 820, a first focus lens 824, and a first reflector 826 and a second reflector 836. The reflectors 826, 836 can be glass and may or may not have a coating. In some examples, the beam splitter 814 can include a second optional focusing lenses 827, 837. The four ports 821, 822, 823, 832 can include a first port 821 for a laser optical pathway coupled to the laser, a second port 822 for a first feedback optical pathway to the spectroscopy system, a third port 823 for a common optical pathway 130 for transmitting both the laser and the optical response signal 119 between the beam splitter 814 and the distal end of the working probe 113, and a fourth port for a second feedback optical pathway to the spectroscopy system. In operation, the laser energy is coupled from the first port 821 to the third port 823 via the collimation lens 820, the reflectors 826, 836, and the first focus lens 824. The optical response signal 119 can be coupled from the third port 823 to the second port 822 via a combination of the focus lens 824 and the first reflector 826. The optical response signal can also be coupled from the third port 823 to the fourth port 832 via a combination of the focus lens 824 and the second reflector 836. The system can include an optical coupler 830 to couple the first and second feedback optical pathways to provide the optical response signal 119. The illustrated example of FIG. 8 can allow efficient coupling of the laser beam with the common optical pathway 130 when the reflectors are glass. At the same time, having two glass reflectors can allow collecting more energy from the response optical path than using a single reflector, thus, resulting in a stronger optical response signal 119. In certain examples, the reflectors can include an opening and can be used a similar fashion as the lone reflector 726 in FIG. 7. The openings can allow the laser energy to pass unobstructed and the two glass reflectors can capture the optical response energy from the collimated light about the laser beam.

Figure 9:
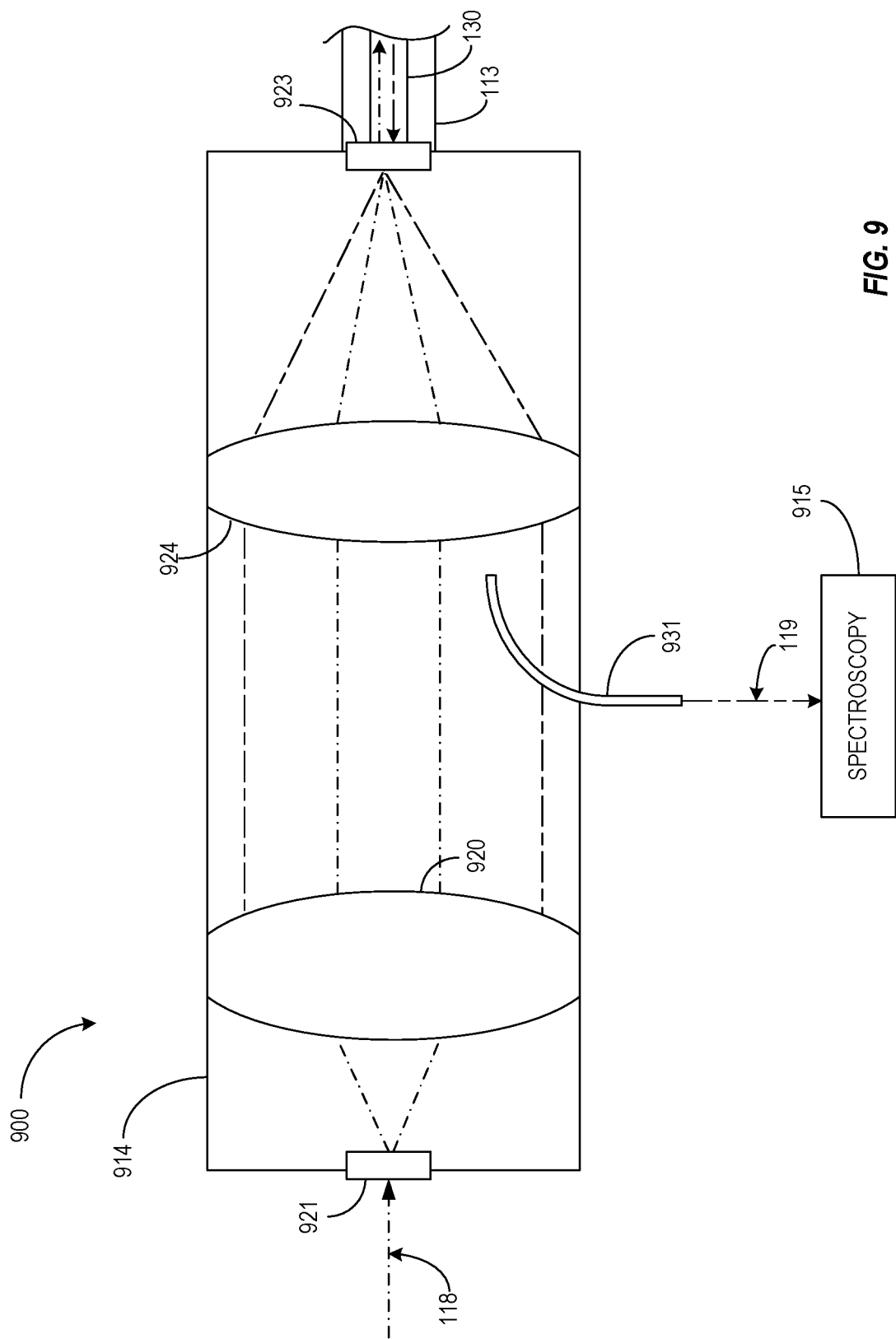
FIG. 9 illustrates generally an example of a beam splitter within an example target identification system.

FIG. 9 illustrates generally a detailed view of an example of a target identification system 900. The target identification system 900 can include a beam splitter 914, a working probe 113, and a spectroscopy system 915. The beam splitter 914 can include at least two ports 921, 923, a collimation lens 920, a focus lens 924, and one or more feedback fibers 931. The feedback fibers or multiple bundles of fibers can receive optical response energy and provide an optical pathway for the optical response energy or signal 919 to be received at the spectroscopy system 915. The two ports 921, 923 can include a first port 921 for a laser optical pathway coupled to the laser, and a second port 923 for a common optical pathway 130 for transmitting both the laser and an optical response signal 119 between the beam splitter 914 and the distal end of the working probe 113. In operation, the laser energy is coupled from the first port 921 to the third port 923 via the collimation lens 920, and the first focus lens 924. As discussed above, the optical response signal 119 can be coupled from the third port 923 to the spectroscopy system via a combination of the focus lens 924 and the feedback fiber(s) 931. In certain examples, the diameter and numerical aperture of the optical pathway at the second port 923 can be larger than the diameter and numerical aperture of the optical pathway providing the laser beam at the first port 921. The size relationship of the optical ports and numerical aperture can allow the optical response signal 119 through the beam splitter to be expanded farther than the optical signal of the laser beam 118. As such, more light from the optical response can be collected without affecting the path of the laser beam compared to a path of the optical response that has less expansion. In certain examples, additional feedback fibers 931 can be placed about the collimated path of the laser between the collimation lens 920 and the focus lens 924 to collect more energy of the optical response signal 919 within the optical splitter. In the extreme, an assembly of feedback fibers 931, for example, in the shape of a ring, can be placed about the path of the laser light to collect all the light of the optical response signal.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method of providing therapeutic treatment of an anatomical target, the method comprising:
   (a) delivering a light beam, generated by a light source, to the anatomical target via a first optical path in a probe;
   (b) in response to the delivery of the light beam to the anatomical target, collecting an optical response signal from the anatomical target and passing the optical response signal through a second optical path, at least a portion of the second optical path being defined by a beam splitter and the portion of the second optical path that is defined by the beam splitter being different from the first optical path;
   (c) redirecting at least a portion of the optical response signal to an optical detection system;
   (d) based at least in part on the redirected at least a portion of the optical response signal, identifying a characteristic of the anatomical target; and
   (e) controlling an energy source to deliver a therapeutic beam, different from the light beam, to treat the anatomical target in accordance with the identified characteristic of the anatomical target.

2. The method of claim 1, comprising extracting spectral information from the optical response signal using the optical detection system,
   wherein identifying the characteristic of the anatomical target is based at least in part on the extracted spectral information.

3. The method of claim 1, wherein the characteristic of the anatomical target includes at least one of a type, a material, a composition, a composition profile, a structure or hardness of the anatomical target.

4. The method of claim 1, further comprising:
   iteratively performing steps (a)-(d) to identify an updated characteristic of the anatomical target; and
   adjusting a parameter associated with the delivered therapeutic beam based at least in part on the updated characteristic of the anatomical target.

5. The method of claim 4, wherein the parameter associated with the delivered therapeutic beam includes at least one of an operation mode, an output power, a pulse frequency, a pulse shape, or a pulse profile.

6. The method of claim 4,
wherein the characteristic of the anatomical target being identified includes respective characteristics of various portions of the anatomical target,
wherein adjusting the parameter associated with the delivered therapeutic beam includes adjusting respective output settings for treating the various portions of the anatomical target.

7. The method of claim 1, wherein the at least a portion of the optical response signal is redirected to the optical detection system using a first reflector included in a beam splitter optically coupled to the probe.

8. The method of claim 7, further comprising merging the second optical path and a third optical path using a second reflector serially positioned with the first reflector along the second optical path.

9. The method of claim 7, wherein the therapeutic beam is directed through an aperture on the first reflector such that the therapeutic beam passes through the second optical path unobstructedly.

10. The method of claim 1, wherein the anatomical target being treated includes one or more of a biological material, hard and soft tissue, or a calculi structure.

11. An apparatus for providing therapeutic treatment of an anatomical target, the apparatus comprising:
a light source for delivering a light beam to the anatomical target via a first optical path in a probe;
a beam splitter defining at least a portion of a second optical path, the portion of the second optical path defined by the beam splitter being different from the first optical path, the beam splitter configured to:
in response to the delivery of the light beam to the anatomical target, collect an optical response signal from the anatomical target and pass the optical response signal through at least a portion of the second optical path; and
redirect at least a portion of the optical response signal;
an optical detection system for receiving the redirected at least a portion of the optical response signal; and
a controller configured to:
based at least in part on the redirected at least a portion of the optical response signal, identify a characteristic of the anatomical target; and
control an energy source to deliver a therapeutic beam, different from the light beam, to the anatomical target in accordance with the identified characteristic of the anatomical target.

12. The apparatus of claim 11, wherein the optical detection system is configured to extract spectral information from the optical response signal,
wherein the controller is configured to identify the characteristic of the anatomical target based at least in part on the extracted spectral information.

13. The apparatus of claim 11, wherein the characteristic of the anatomical target includes at least one of a type, a material, a composition, a composition profile, a structure or hardness of the anatomical target.

14. The apparatus of claim 11, wherein the optical detection system is configured to receive an updated optical response signal, and the controller is further configured to (i) identify an updated characteristic of the anatomical target based on the updated optical response signal and (ii) cause adjustment of a parameter associated with the delivered therapeutic beam based at least in part on the updated characteristic of the anatomical target.

15. The apparatus of claim 14, wherein the parameter associated with the delivered therapeutic beam includes at least one of an operation mode, an output power, a pulse frequency, a pulse shape, or a pulse profile.

16. The apparatus of claim 14,
wherein the characteristic of the anatomical target being identified includes respective characteristics of various portions of the anatomical target,
wherein the controller is further configured to adjust the parameter associated with the delivered therapeutic beam by adjusting respective output settings for treating the various portions of the anatomical target.

17. The apparatus of claim 11, wherein the beam splitter comprises a first reflector optically coupled to the probe for redirecting the at least a portion of the optical response signal.

18. The apparatus of claim 17, wherein the beam splitter further comprises a second reflector serially positioned with the first reflector along the second optical path for merging the second optical path and a third optical path.

19. The apparatus of claim 17, wherein the first reflector includes an aperture thereon, the therapeutic beam being directed through the aperture such that the therapeutic beam passes through the second optical path unobstructedly.

20. The apparatus of claim 11, wherein the anatomical target being treated includes one or more of a biological material, hard and soft tissue, or a calculi structure.

* * * * *

UNITED STATES PATENT AND TRADEMARK OFFICE
CERTIFICATE OF CORRECTION

| | | |
|---|---|---|
| PATENT NO. | : 12,220,166 B2 | Page 1 of 1 |
| APPLICATION NO. | : 18/332072 | |
| DATED | : February 11, 2025 | |
| INVENTOR(S) | : Bukesov et al. | |

It is certified that error appears in the above-identified patent and that said Letters Patent is hereby corrected as shown below:

On the Title Page

On page 3, in Column 2, item (56) under "Other Publications", Line 15, delete "Opitcal" and insert --Optical-- therefor Signed and Sealed this
Nineteenth Day of August, 2025

Coke Morgan Stewart
*Acting Director of the United States Patent and Trademark Office*